US011690794B2

(12) United States Patent
Ronan et al.

(10) Patent No.: US 11,690,794 B2
(45) Date of Patent: Jul. 4, 2023

(54) SULFATE-FREE FORMULATIONS

(71) Applicant: RHODIA OPERATIONS, Paris (FR)

(72) Inventors: Mary Ronan, Langhorne, PA (US); Rajesh Patel, Pennington, NJ (US)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/896,370

(22) Filed: Feb. 14, 2018

(65) Prior Publication Data

US 2018/0263879 A1 Sep. 20, 2018

Related U.S. Application Data

(60) Provisional application No. 62/459,757, filed on Feb. 16, 2017.

(51) Int. Cl.
| | | |
|---|---|---|
| *C11D 1/88* | (2006.01) | |
| *C11D 1/94* | (2006.01) | |
| *A61K 8/44* | (2006.01) | |
| *A61K 8/42* | (2006.01) | |
| *A61Q 19/10* | (2006.01) | |
| *A61K 8/49* | (2006.01) | |
| *A61K 8/46* | (2006.01) | |
| *A61Q 19/00* | (2006.01) | |
| *C11D 1/10* | (2006.01) | |
| *C11D 1/18* | (2006.01) | |
| *C11D 1/83* | (2006.01) | |
| *C11D 3/34* | (2006.01) | |

(52) U.S. Cl.
CPC ............... *A61K 8/442* (2013.01); *A61K 8/42* (2013.01); *A61K 8/44* (2013.01); *A61K 8/463* (2013.01); *A61K 8/49* (2013.01); *A61K 8/4946* (2013.01); *A61Q 19/00* (2013.01); *A61Q 19/10* (2013.01); *C11D 1/10* (2013.01); *C11D 1/18* (2013.01); *C11D 1/83* (2013.01); *C11D 1/88* (2013.01); *C11D 1/94* (2013.01); *C11D 3/34* (2013.01); *A61K 2800/30* (2013.01)

(58) Field of Classification Search
CPC .... C11D 1/10; C11D 1/18; C11D 1/37; C11D 3/72; C11D 3/83; C11D 1/88; C11D 1/94; C11D 3/32; C11D 3/34
USPC ....... 510/123, 124, 126, 130, 136, 137, 138, 510/499, 501, 505, 506
See application file for complete search history.

(56) References Cited

U.S. PATENT DOCUMENTS

| | | |
|---|---|---|
| 7,410,649 B2 | 8/2008 | Yoshimi et al. |
| 2005/0158270 A1* | 7/2005 | Frantz .................... A61K 8/375 424/70.24 |
| 2008/0009429 A1 | 1/2008 | Klug et al. |
| 2010/0158964 A1* | 6/2010 | Cunningham ....... A61K 8/0208 424/402 |
| 2011/0123465 A1* | 5/2011 | Walters .................. A61K 8/442 424/49 |
| 2011/0232668 A1 | 9/2011 | Hoffmann et al. |
| 2012/0213725 A1 | 8/2012 | Galleguillos et al. |
| 2014/0039066 A1 | 2/2014 | Grimadell et al. |
| 2014/0349902 A1* | 11/2014 | Allef ....................... A61K 8/361 510/119 |
| 2015/0044157 A1 | 2/2015 | Kulkarni et al. |
| 2015/0125415 A1* | 5/2015 | Klug ...................... A61K 47/20 424/70.19 |
| 2015/0335555 A1 | 11/2015 | Dobrowolski et al. |
| 2016/0264561 A1* | 9/2016 | Giles ........................ C11D 1/58 |
| 2016/0271034 A1 | 9/2016 | Fevola et al. |

FOREIGN PATENT DOCUMENTS

CN 106265314 A 1/2017

OTHER PUBLICATIONS

BASF, Iris Hutter, Jessica Erasmy, Norbert Boyxen, "Looking for 'green' alternatives in skin cleansing? New concepts—mild & easy to formulate" article Mar. 21, 2013.
Galaxy Surfactants Ltd., "Galsoft® GLI21 Ultra Mild Cleanser" article 2015.
Stepan "Stepan Sulfate-Free Surfactant Solutions" article 2013.
"Clariant; Taking care of your formulations Edition 2001—Shower Gel A I /8091".
Database GNPD [Online] MINTEL; Aug. 13, 2013 (Aug. 13, 2013), anonymous: "Pharma Citrus Restructuring Shampoo", XP055742598.

\* cited by examiner

*Primary Examiner* — Gregory R Delcotto
(74) *Attorney, Agent, or Firm* — Vorys, Sater, Seymour and Pease LLP; Anthony P. Venturino; Maryellen Feehery Hank

(57) ABSTRACT

An aqueous personal care composition comprising: one or more amphoacetates; one or more glutamate surfactants selected from sodium lauroyl glutamate, dipotassium cocoyl glutamate, potassium lauryl/myristoyl glutamate and combinations thereof; and cocamide MIPA; wherein the composition is free of sulfates and ethoxylates.

17 Claims, No Drawings

SULFATE-FREE FORMULATIONS

CROSS-REFERENCE TO RELATED APPLICATION

The present application claims the benefit of priority under 35 U.S.C. § 119(e) of U.S. Provisional Application Ser. No. 62/459,757, filed on Feb. 16, 2017, the entire disclosure of which is incorporated herein by reference.

BACKGROUND

At the present time, most of the commercially available personal care compositions are based on sulfate-containing surfactants such as sodium lauryl sulfate, (SLS), ammonium lauryl sulfate (ALS), sodium laureth sulfate (SLES) or ammonium laureth sulfate (ALES). SLS, ALS, SLES and ALES are the most widespread sulfate-containing surfactants used in this field as they are inexpensive and as they exhibit at the same time satisfactory cleansing and foaming properties. Another advantage is that they can be easily thickened by the addition of common salt such as sodium chloride.

However personal care compositions including sulfate-containing surfactants also present significant drawbacks. As a matter of fact sulfate-containing surfactants such as SLS are known to be liable to give rise to tolerance problems, especially on the skin and the eyes. Another drawback of sulfate-containing surfactants is their tendency to strip the skin, scalp or hair of its natural oils, fats or proteins contained at their surface. In the long term the repeated use of personal care compositions including sulfate-containing surfactants may therefore cause irritation to the skin or scalp and/or give damage on hair fibers.

Moreover, certain markets have a negative bias towards many ethoxylated materials, like SLES.

In recent times there is thus an increasing demand for personal care compositions including safe, environment friendly, and/or milder surfactants, and especially for personal care compositions free of both sulfate-containing surfactants and ethoxylates. One of the major challenges of formulating sulfate-free/ethoxylate-free personal care compositions lies in the need to maintain mildness, satisfactory cleansing, conditioning and foaming properties without negatively impacting viscosity of the overall composition. For example, sulfate-free and ethoxylate-free formulations typically require thickening polymers to reach the desired viscosity. Unfortunately, these polymers adversely affect the sensory profile of the formulation, such as the feel and foam production.

SUMMARY

The present disclosure provides formulations of surfactants, which can be adjusted to a pH range sufficient to reach the desired viscosity without the use of thickening polymers and without affecting the sensory profile.

DETAILED DESCRIPTION

In general, compositions according to the present disclosure include one or more glutamate surfactants selected from sodium lauroyl glutamate, dipotassium cocoyl glutamate, dipotassium lauroyl/myristoyl glutamate and combinations thereof; one or more amphoacetates; and cocamide MIPA; wherein the composition is free of sulfates and ethoxylates. In an embodiment, the formulation is mild and produces a creamy foam. In an embodiment, the combination of surfactants is thickened at a pH of 5 to 6.

By the expressions "sulfate-containing surfactants free composition" or "sulfate-free composition" or "free of sulfates" it is meant that the composition of the disclosure is devoid of, i.e. does not contain (0%) any anionic surfactant which is a derivative of a sulfate, such as especially sodium lauryl sulfate (SLS), sodium laureth sulfate (SLES), ammonium lauryl sulfate (ALS) or ammonium laureth sulfate (ALES).

For the purposes of the present disclosure, the term "anionic surfactant which is a derivative of a sulfate" means surfactants comprising at least one anionic group or group that can be ionized into an anionic group, chosen from sulfate functions ($—OSO_3H$ or $—OSO_3—$). Thus, the following anionic surfactants are preferably not present in the composition according to the disclosure: salts of alkyl sulfates, of alkylamide sulfates, of alkyl ether sulfates, of alkylamido ether sulfates, of alkylaryl ether sulfates, of monoglyceride sulfates.

As used herein, the terms "ethoxylate free" and "free of ethoxylates" refers to a composition, mixture, or ingredients that do not contain alcohol ethoxylates, alkyl phenol ethoxylates or phenol-containing compounds or to which the same has not been added. Should alcohol ethoxylates, alkyl phenol ethoxylates or alkyl phenol ethoxylate-containing compounds be present through contamination of a composition, mixture, or ingredients, the amount of the same shall be less than 0.5 wt. %. In another embodiment, the amount of is less than 0.1 wt. % and in yet another embodiment, the amount is less than 0.01 wt. %.

By the expression "composition having a satisfactory viscosity" or "desired viscosity" it is meant here a composition that has an apparent viscosity comprised between 1,500 and 50,000 cps, for instance comprised between 2,000 and 30,000 cps, for instance comprised between 3,000 and 25,000 cps. The apparent viscosity can be measured after 24 hours in a temperature-controlled room (21±3° C.), using a Brookfield Viscosimeter Model DV-II+ at 10 RPM, with a RV spindle 4 or 5. The viscosity value can be taken after a stabilization time of 1 min.

By the expression "foaming properties" it is meant especially here flash foam and foam volume, which are among the main factors affecting the consumer perception about the foam quality. Well-known tests may be used to measure these factors.

The composition of the present disclosure is a personal care composition, preferably a personal care cleansing composition, that is to say a composition aimed to the washing/cleaning and in particular for a body-care application, such as but not limited to a shower gel, a facial cleanser, a body-wash, a liquid hand soap, a shampoo or a cleansing conditioner.

For the avoidance of any doubt the amounts of surfactant refer to the actual amount of active surfactant compound present in the composition. In other words, it does not include the residue which may be present as an impurity in a commercially available surfactant mixture.

In an embodiment, certain combinations of particular sulfate-free anionic surfactants and ethoxylate-free materials are used in the surfactant system of the compositions of the present disclosure.

Compositions of the present disclosure include one or more glutamate surfactants that are mono- or di-carboxylate salts (e.g., sodium, potassium, ammonium and TEA) of N-acylated glutamic acid. In an embodiment, the glutamate surfactant(s) are selected from sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, potassium myristoyl glutamate, dipotassium cocoyl glutamate, dipotassium lauroyl/myristoyl glutamate and combinations thereof. In another embodiment, the one or more glutamate surfactants are selected from sodium lauroyl glutamate, dipotassium cocoyl glutamate, dipotassium lauroyl/myristoyl glutamate and combinations thereof. In an embodiment, the one or more glutamate surfactants are present in an amount from about 3 wt % to about 5 wt % based upon the total weight of the composition.

Compositions of the present disclosure also include one or more amphoacetates. In an embodiment, the amphoacetate is selected from amphoacetates of formula:

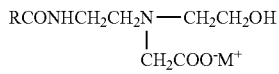

where R is an aliphatic group of 8 to 22 carbon atoms and M is a cation such as sodium, potassium, ammonium or substituted ammonium. In an embodiment, the amphoacetate is selected from sodium lauroamphoacetate (e.g. Miranol® Ultra L32), sodium cocoamphoacetate (e.g. Miranol® Ultra L-99), and combinations thereof. In an embodiment, the amphoacetate is present in an amount from about 8 wt % to about 12 wt % based upon the total weight of the composition.

Compositions of the present disclosure further include one or more alkanolamide surfactants. Alkanolamide surfactants include, for example, acetamide MEA, cocamide DEA, cocamide MEA, cocamide methyl MEA, cocamide MIPA, hydroxystearamide MEA, PEG-5 cocamide MEA, lactamide MEA, lauramide MEA and lauramide DEA, preferably cocamide MIPA or cocamide methyl MEA. In another embodiment, the one or more alkanolamide surfactants are present in an amount from about 1 wt % to about 3 wt % based upon the total weight of the composition.

In an embodiment, one or more pH adjusting agents are added to the composition to reach a desired viscosity at room temperature. In an embodiment, pH adjusting agents are selected from citric acid, succinic acid, phosphoric acid, sodium hydroxide, sodium carbonate, and combinations thereof. In an embodiment, the pH of the composition is about 5 to about 6.

Optionally, any of the compositions of the present disclosure includes a methyl oleoyl taurate of formula $R^a CON(CH_3)CH_2CH_2SO_3X^a$, in which $R^a$ is the hydrocarbon radical of oleic acid and $X^a$ is a counterion. The counterion $X^a$ of methyl oleoyl taurate may be an alkali metal ion, alkaline earth metal ion or ammonium ion.

The counterion $X^a$ of methyl oleoyl taurate is typically an alkali metal ion, in particular a sodium ion. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, di ethanol ammonium and triethanolammonium.

In an embodiment, the composition is a body wash that includes potassium lauroyl/myristoyl glutamate, sodium cocoamphoacetate, cocamide MIPA, and sodium methyl oleoyl taurate.

In another embodiment, the composition is a baby wash that includes sodium lauroyl glutamate, sodium lauroamphoacetate, cocamide MIPA, and PEG-80 sorbitan laurate.

The compositions of the present disclosure may further include additional optional ingredients which may bring specific benefits for the intended use. Such optional ingredients may include colorants, pearlescent agents, emollients, hydrating agents, opacifiers, and preservatives. The skilled person is able to select according to general knowledge in the art of formulating personal care compositions such as shampoos, shower gels and liquid hand soaps, and the vast literature there-related, appropriate such optional ingredients for application purposes.

In one embodiment, the composition of the present disclosure further includes one or more benefit agents, such as emollients, moisturizers, conditioners, skin conditioners, or hair conditioners such as silicones such as volatile silicones, gums or oils, or non-amino silicones and mixtures thereof, mineral oils, vegetable oils, including *arachis* oil, castor oil, cocoa butter, coconut oil, corn oil, cotton seed oil, olive oil, palm kernel oil, rapeseed oil, safflower seed oil, sesame seed oil and soybean oil, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, eicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A, C, D, E, K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; dyes; hair coloring agents; bleaching agents; hair bleaching agents; UV absorbers, such as benzophenone, bornelone, PABA (Para Amino Benzoic Acid), butyl PABA, cinnamidopropyl trimethyl ammonium chloride, disodium distyrylbiphenyl disulfonate, potassium methoxycinnamate; anti-UV agents, such as butyl methoxydibenzoylmethane; octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin-coloring agents, such as dihydroxyacetone; liporegulators; weight-reduction agents; anti-acne agents; antiseborrhoeic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as *alnus, arnica, artemisia capillaris, asiasarum* root, *calendula*, chamomile. *Cnidium*, comfrey, fennel, galla rhois, hawthorn, houttuynia, hypericum, jujube, kiwi, licorice, *magnolia*, olive, peppermint, *philodendron, salvia, sasa albomarginata*, imidazoles such as ketoconazole and elubiol, those anti-acne agents described in Gollnick, H. et al. 196(1) Dermatology Sebaceous Glands, Acne and Related Disorders, 119-157 (1998), which is incorporated by reference herein to the extent that it is not inconsistent with the present application; refreshing agents; cicatrizing agents; vascular-protection agents; agents for the reduction of dandruff, seborrheic dermatitis, or psoriasis, such as zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, ciclopirox olamine, anti-psoriasis agents such as vitamin D analogs, e.g. calcipotriol, calcitriol, and tacaleitrol, vitamin A analogs such as esters of vitamin A including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; reducing agents for permanent-waving; reflectants, such as mica, alumina, calcium silicate, glycol dioleate, glycol distearate, silica, sodium magnesium fluorosilicate; essential oils and fragrances.

In one embodiment, the personal care composition of the present invention includes from about 0.1 to about 50 wt %, more typically from about 0.3 to about 25 wt %, and still more typically from about 0.5 to 10 wt %, based upon total weight of the composition and independently for each such ingredient, of one or more benefit agents.

Compositions according to the present disclosure may optionally further include other ingredients, such as, for example, preservatives such as benzyl alcohol, methyl paraben, propyl paraben, imidazolidinyl urea, sodium benzoate, potassium sorbate, salicylic acid, methylchloroisothiazolinone and methylisothiazolinone, thickeners such as high molecular weight crosslinked polyacrylic acid (carbomer), PEG diester of stearic acid and the like, and viscosity modifiers such as block polymers of ethylene oxide and propylene oxide, electrolytes, such as sodium chloride, sodium sulfate, and polyvinyl alcohol, perfumes, dyes, and sequestering agents, such as disodium ethylenediamine tetra-acetate. In general, personal care compositions may optionally include, based on total weight of the personal care composition and independently for each such ingredient, up to about 10 wt %, preferably from 0.5 wt % to about 5.0 wt %, of such other ingredients, depending on the desired properties of the personal care composition.

Compositions of the present disclosure are used in a manner known in the art, for example, in the case of a cleanser or shampoo, by application of the cleanser or shampoo to the skin and/or hair and optionally rinsing the cleanser or shampoo off of the skin and/or hair with water.

According to any one of the embodiments, compositions of the present disclosure may be prepared using a concentrated flowable surfactant composition.

The disclosure is also directed toward concentrates that are suitable to prepare a composition of the present disclosure.

Concentrates including a mixture of surfactants and/or conditioning agents are advantageous as their use would reduce the need to transport a plurality of individual components.

Personal care compositions are usually prepared by mixing individual surfactants and conditioning agents. These components may be supplied as concentrated solutions which are diluted and/or and combined in appropriate ratios by the formulator. The present disclosure covers any surfactant concentrate to be used as component ingredient to prepare a composition of the disclosure, and especially to surfactant concentrates containing limited levels of water (more advantageous from a cost and environmental perspective).

While specific embodiments are discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

The present disclosure will further be described by reference to the following examples. The following examples are merely illustrative and are not intended to be limiting.

EXAMPLES

The following sulfate-free, ethoxylate-free compositions were prepared.

The starting materials used are identified by the INCI names and/or by the commercial references. All ingredients are expressed by weight percent of the total formulation.

Example 1

TABLE 1

| Formulation I. | | |
|---|---|---|
| Material | Wt % | Active Wt % |
| Geropon ® PCG (Potassium Lauroyl/Myristoyl Glutamate) | 17.9 | 5.0 |
| Miranol ® Ultra L32 (Sodium Lauroamphoacetate) | 40.0 | 12.0 |
| Mackamide ® CPA (Cocamide MIPA) | 1.00 | 1.0 |
| Kathon ®CG (Methylchloroisothiazolinone, Methylisothiazolinone) | 0.10 | |
| De-ionized water | 41.0 | |
| Citric Acid | QS | |

Formulation Procedure: Charge Miranol® Ultra L32 to the water and begin heating to 65° C. Add Geropon® PCG and mix until uniform. Charge Mackamide® CPA and mix until uniform. Once uniform, cool the formula to 35° C. Adjust if necessary to pH 5-6. Formulation I exhibited a viscosity of 11,110 cps (measured using a Brookfield Viscosimeter Model DV-II+ at 10 RPM, with a RV spindle 4) and pH 5.5 without the use of thickening polymers.

Example 2

The amphoteric surfactant used in Formulation I (Miranol® Ultra L32) was replaced with other amphoteric surfactants shown in Table 2 and viscosity was re-evaluated each time. Results are presented below in Table 2.

TABLE 2

| Replacement amphoteric surfactants in Formulation I. | |
|---|---|
| Amphoteric Surfactant | Viscosity (cps) |
| Miranol ® Ultra L32 (Sodium Lauroamphoacetate) (Example 1) | 11,110 |
| Miranol ® Ultra L-99 (Sodium Cocoamphoacetate) | 5,600 |
| Mackam ® CBS 50G (Cocamidopropyl Hydroxysultaine) | Water-like (about 1) |
| Mackam ® 2S (Disodium Soyamphodiacetate) | Water-like (about 1) |
| Mackam ® 2CSF40CG (Disodium Cocoamphodipropionate) | Water-like (about 1) |
| Mirataine ® BET C 30 (Cocamidpropyl Betaine) | Water-like (about 1) |

Example 3

An adult body wash formulation was prepared using the materials listed below in Table 3. All ingredients are expressed by weight percent of the total formulation. Formulation II exhibited a viscosity of 7,000-15,000 cps (measured using a Brookfield Viscosimeter Model DV-II+ at 10 RPM, with a RV spindle 4) without the use of thickening polymers.

TABLE 3

| Formulation II. | | |
|---|---|---|
| Material | Wt % | Active Wt % |
| Geropon ® PCG (Potassium Lauroyl/Myristoyl Glutamate) | 10.70 | 3.0 |
| Miranol ® Ultra L-99 (Sodium Cocoamphoacetate) | 40.00 | 12.0 |
| Mackamide ® CPA (Cocamide MIPA) | 1.00 | 1.0 |
| Geropon ® T77 (Sodium Methyl Oleoyl Taurate) | 1.00 | 0.77 |
| DI water | 38.60 | |
| Fragrance | 0.50 | |
| Glycerin | 2.00 | |
| Citric Acid | QS | |
| Sodium Benzoate | 0.40 | |

Example 4

A baby wash formulation was prepared using the materials listed below in Table 4. All ingredients are expressed by weight percent of the total formulation. Formulation III exhibited a viscosity of 3,000-4,000 cps (measured using a Brookfield Viscosimeter Model DV-II+ at 10 RPM, with a RV spindle 4) without the use of thickening polymers.

TABLE 4

| Formulation III. | | |
|---|---|---|
| Material | Wt % | Active Wt % |
| Sodium Lauroyl Glutamate | 10.71 | 3.0 |
| Miranol ® Ultra L32 (Sodium Lauroamphoacetate) | 33.33 | 10.0 |
| Mackamide ® CPA (Cocamide MIPA) | 1.00 | 1.0 |
| Alkamuls ® PSML-80/72LD (PEG-80 Sorbitan Laurate) | 1.00 | 0.72 |
| DI water | 51.75 | |
| Fragrance | 0.20 | |
| Glycerin | 2.00 | |
| Citric Acid | QS | |
| Sodium Benzoate | 0.40 | |

The disclosed subject matter has been described with reference to specific details of particular embodiments thereof. It is not intended that such details be regarded as limitations upon the scope of the disclosed subject matter except insofar as and to the extent that they are included in the accompanying claims.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments described herein. The exemplary embodiments described herein illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components, substances and steps. The terms "consists of" or "consisting of" in relation to the surfactant system of the composition of the present disclosure are used here to mean that the composition comprises a surfactant system which is strictly formed of a mixture of the surfactants that are expressly recited, and contains no other surfactants. As used herein the term "consisting essentially of" shall be construed to mean including the listed components, substances or steps and such additional components, substances or steps which do not materially affect the basic and novel properties of the composition or method. In some embodiments, a composition in accordance with embodiments of the present disclosure that "consists essentially of" the recited components or substances does not include any additional components or substances that alter the basic and novel properties of the composition. If there is any conflict in the usages of a word or term in this specification and one or more patent or other documents that may be incorporated herein by reference, the definitions that are consistent with this specification should be adopted.

We claim:

1. An aqueous personal care composition comprising:
   a. one or more amphoacetates;
   b. one or more glutamate surfactants selected from the group consisting of sodium lauroyl glutamate, dipotassium cocoyl glutamate, potassium lauroyl/myristoyl glutamate and combinations thereof; and
   c. cocamide MIPA;
   wherein the composition is free of sulfates and contains less than 0.5 wt % of alcohol ethoxylates, alkyl phenol ethoxylates and ethyl phenyl ethoxylate containing compounds, wherein the composition has a viscosity of 7,000-15,000 cps measured using a Brookfield Viscometer Model DV-II+ at 10 rpm with a TV spindle 4.

2. The composition of claim 1, wherein the pH ranges from 5 to 6.

3. The composition of claim 1, wherein the amphoacetate is sodium lauroamphoacetate.

4. The composition of claim 3, wherein the sodium lauroamphoacetate is present in an amount of about 8 to about 12 weight percent based upon the total weight of the composition.

5. The composition of claim 1, wherein the dipotassium cocoyl glutamate is present in an amount of about 3 to about 5 weight percent based upon the total weight of the composition.

6. The composition of claim 1, wherein the cocamide MIPA is present in an amount of about 1 to about 3 weight percent based upon the total weight of the composition.

7. The composition of claim 1, wherein the composition is a body wash.

8. The composition of claim 1, wherein the composition is a baby wash comprising sodium lauroyl glutamate, sodium lauroamphoacetate, cocamide MIPA, and PEG-80 sorbitan laurate.

9. The composition of claim 8, wherein the pH ranges from 5 to 6.

10. The composition of claim 8, wherein the sodium lauroamphoacetate is present in an amount of about 8 to about 12 weight percent based upon the total weight of the composition.

11. The composition of claim 8, wherein the dipotassium cocoyl glutamate is present in an amount of about 3 to about 5 weight percent based upon the total weight of the composition.

12. The composition of claim 8, wherein the cocamide MIPA is present in an amount of about 1 to about 3 weight percent based upon the total weight of the composition.

13. An aqueous personal care composition comprising:
   potassium lauroyl/myristoyl glutamate,
   sodium cocoamphoacetate, and
   cocamide MIPA,
   sodium methyl oleoyl taurate,
   wherein the composition is free of sulfates and contains less than 0.5 wt. % of alcohol ethoxylates, alkyl phenol ethoxylates and ethyl phenyl ethoxylate containing compounds, wherein the composition has a viscosity of 7,000-15,000 cps measured using a Brookfield Viscometer Model DV-II+ at 10 rpm with a TV spindle 4.

14. The composition of claim 3, wherein the glutamate surfactant is potassium lauroyl/myristoyl glutamate.

15. The composition of claim 2, wherein the amphoacetate is sodium lauroamphoacetate and the glutamate surfactant is sodium lauroyl glutamate.

16. The composition of claim 2, wherein the amphoacetate is sodium lauroamphoacetate and the glutamate surfactant is dipotassium cocoyl glutamate.

17. The composition of claim 2, wherein the amphoacetate is sodium lauroamphoacetate and the glutamate surfactant is potassium lauroyl/myristoyl glutamate.

* * * * *